United States Patent [19]
Karageozian et al.

[11] Patent Number: 5,866,120
[45] Date of Patent: Feb. 2, 1999

[54] METHOD FOR ACCELERATING CLEARANCE OF HEMORRHAGIC BLOOD FROM THE VITREOUS HUMOR WITH HYALURONIDASE

[75] Inventors: Hampar L. Karageozian; Vicken H. Karageozian, both of San Juan Capistrano; Maria Christina Kenney, Malibu, all of Calif.; Jose Luis Gutierrez Flores; Gabriel Arturo Carpio Aragon, both of Tijuana, Mexico; Anthony B. Nesburn, Malibu, Calif.

[73] Assignee: Advanced Corneal Systems, Inc., Irvine, Calif.

[21] Appl. No.: 561,636

[22] Filed: Nov. 22, 1995

[51] Int. Cl.$^6$ .......................... A61K 38/43; A61K 38/46; C12N 9/26
[52] U.S. Cl. .......................... 424/94.62; 424/94.1; 514/2; 514/912; 435/201
[58] Field of Search .............................. 424/94.1, 94.62, 424/94.64, 94.67, 535, 601; 514/2, 53, 912; 435/201

[56] References Cited

U.S. PATENT DOCUMENTS

| | | | |
|---|---|---|---|
| 3,869,548 | 3/1975 | Dabis | 424/94 |
| 4,141,973 | 2/1979 | Balazs | 424/180 |
| 4,174,389 | 11/1979 | Cope | 424/94 |
| 4,474,751 | 10/1984 | Haslam et al. | 424/78 |
| 4,757,089 | 7/1988 | Epstein | 514/571 |
| 4,820,516 | 4/1989 | Sawyer et al. | 424/94.62 |
| 4,861,760 | 8/1989 | Mazuel et al. | 514/54 |
| 4,871,742 | 10/1989 | Bonne et al. | 514/262 |
| 5,077,033 | 12/1991 | Viegas et al. | 514/668 |
| 5,166,331 | 11/1992 | della Valle et al. | 536/55.1 |
| 5,252,318 | 10/1993 | Joshi et al. | 424/78.04 |
| 5,260,059 | 11/1993 | Acott et al. | 424/94.67 |
| 5,270,051 | 12/1993 | Harris | 424/427 |
| 5,292,509 | 3/1994 | Hageman | 424/94.61 |
| 5,300,295 | 4/1994 | Viegas et al. | 424/427 |
| 5,318,780 | 6/1994 | Viegas et al. | 424/427 |
| 5,326,761 | 7/1994 | Rozier | 514/235.8 |

FOREIGN PATENT DOCUMENTS 0193330  9/1986  European Pat. Off. .

OTHER PUBLICATIONS

Machemer, M.D., Robert and Norton, M.D., Edward W.D., Experimental Retinal Detachment in the Owl Monkey, vol. 66, No. 3 (pp. 388–427).
Foulds, Wallace S., Allan, Donald, Moseley, Harry, and Kyle, Peter M., Effect of Intravitreal Hyaluronidase on the Clearance of Tritiated Water from the Vitreous to the Choroid, British Journal of Ophthalmology, 1985, 69: 529–532.
O'Neill, M.B., R. and Shea, M.B., M., The Effects of Bacterial Collagenase in Rabbit Vitreous, Canad J. Ophthal 8:366–370, 1973.
Antoszyk, Andrew N.; Gottlieb, Justin L.; Casey, Raynor C.; Hatchell, Diane L.; and McChemer, Robert, An Experimental Model of Preretinal Neovascularization in the Rabbit—Investigative Ophthalmology & Visual Science, vol. 32, No. 1, Jan. 1991 (pp. 46–52).
Hageman, Gregory S.; and Johnson Lincoln V., Chondroitin 6–Sulfate Glycosaminoglycan is a Major Constituent of Primate Cone Photoreceptor Matrix Sheaths, vol. 6, No. 4, 1987 pp. 639–646.
Skrzypczak–Spak, M.D., K.E., and Dresden, PH.D. , Mar., Experimental Liquefaction of the Vitreous Body (pp. 624–630), Ann. Ophthal. 3:624–630, 1971.
Winkler, Ph.D, Barry S. and Cohn, M.D., Edward M., Hyaluronidase and Retinal Function, Arch Ophthalmol—vol. 103, Nov. 1985 (pp. 1743–1746).
Calbiochem Catalog 1994/1995 (6 pgs.).
D. Van Nostrand Company, Inc. Biochemists' Handbook, 1968 (4 pgs.).
Sigma, Biochemicals Organic Compounds (Information Brochure), Diagnostic Reagents (4 pgs.), 1995.
Physicians' Desk Reference, 43rd Edition, 1989 (4 pgs.).
Linder et al. Scand. J. Dent. Res., 79:523–527, 1971.
Kim et al., Korea Univ. Med. J., 9:87–97, and English translation of abstract, 1972.
Belkin et al., Urokinase–Treatment of Fresh Laser Irradiation–Induced Vitreous Hemorrhage, Ophthalmologica, Basel, 187:152–156, 1983.
Chapman–Smith and Crock, Urokinase in the Manageent of Vitreous Heamorrhage, Br. J. Opthalmol., 61:500–505, 1977.
Gottlieb et al., The Safety of Intravitreal Hyaluronidase, Invest. Ophthalmol. Visual Sci. 31:2345–2352, 1990.
Rietschel and Wilson, Ocular Inflammation in Patients Using Soft Contact Lenses, Arch. Dermatol. 118:147, 1982.
Enzyme Nomenclature, Academic Press, Inc., San Diego, CA, 1992.

*Primary Examiner*—David M. Naff
*Assistant Examiner*—Janet M. Kerr
*Attorney, Agent, or Firm*—Sereboff & Buyan, LLP

[57] ABSTRACT

A thimerosal-free hyaluronidase preparation wherein the preferred hyaluronidase enzyme is devoid of molecular weight fractions below 40,000 MW, between 60–70,000 MW and above 100,000 MW. Also disclosed is a method for accelerating the clearance of hemorrhagic blood from the vitreous humor of the eye, comprising the step of contacting at least one hemorrhage-clearing enzyme (e.g., a β-glucuronidase, matrix metalloproteinase, chondroitinase, chondroitin sulfatase or protein kinase) with the vitreous humor in an amount which is effective to cause accelerated clearance of blood therefrom.

9 Claims, 6 Drawing Sheets

| Hyaluronidase Preparation | SPECIFIC ENZYMATIC ACTIVITIES DETERMINED BY ZYMOGRAPHY | | |
|---|---|---|---|
| | Hyaluronic Acid | Gelatin | Casein |
| Hyaluronidase (ACS) | Inactive above 100,000MW | Inactive between 60,000–100,000MW | Inactive above 45,000MW |
| Bovine Hyaluronidase Type VI-S (Sigma) | Active above 100,000MW | Active between 60,000–100,000MW | Active above 45,000MW |
| Ovine Hyaluronidase Type V (Sigma) | Active above 100,000MW | Active between 60,000–100,000MW | Active above 45,000MW |
| Bovine Hyaluronidase Type IV-S | Active above 100,000MW | Active between 60,000–100,000MW | Active above 45,000MW |
| Bovine Hyaluronidase Type I-S | Active above 100,000MW | Active between 60,000–100,000MW | Active above 45,000MW |

FIG.2

Toxic Effect of Single Dose Intravitreal Injection of BSS, BSS + Thimerisol, Hyaluronidase (ACS) and Hyaluronidase (Wydase®) in Rabbits

| Group | Treatment & Dosage (Volume = 100μL) | Results by Day 7 | |
|---|---|---|---|
| | | Fundus Photography Fluorescein Angiography | Histology |
| 1 | BSS | Normal | Normal |
| 2 | BSS + Thimerisol (0.0075mg) | Breakdown of blood-retinal barrier | Retinal necrosis |
| 3 | BSS + (0.025mg) | Severe retinal effects & intravitreal hemorrhage | Severe retinal necrosis |
| 4 | Hyaluronidase (Wydase) - 1 IU | Slight fluoescien leakage. Compromised blood-retinal barrier | No significant change |
| 5 | Hyaluronidase (Wydase) - 15 IU | Severe retinal damage | Equivocal changes |
| 6 | Hyaluronidase (Wydase) - 30 IU | Severe retinal damage | Retinal necrosis |
| 7 | Hyaluronidase (Wydase) - 50 IU | Extensive retinal damage and retinal detechment | Retinal necrosis |
| 8 | Hyaluronidase (Wydase) - 150 IU | Extensive retinal damage and retinal detechment | Severe retinal necrosis |
| 9 | Hyaluronidase (ACS) - 1 IU | Normal | Normal |
| 10 | Hyaluronidase (ACS) - 15 IU | Normal | Normal |
| 11 | Hyaluronidase (ACS) - 30 IU | Normal | Normal |
| 12 | Hyaluronidase (ACS) - 50 IU | Normal | Normal |
| 13 | Hyaluronidase (ACS) - 150 IU | Compromised blood-retinal barrier | Normal |

FIG.3

Hemorrhage Clearing Efficacy of Single-Dose Intravitreal Hyaluronidase (ACS) in the Rabbits
*12 New Zealand Rabbits Are Injected With 10μl or 100μl of Blood in Both Eyes Intravitreally

| Group | Number of Rabbits | Eye Treatments | | Results | |
|---|---|---|---|---|---|
| | | Left Eye | Right Eye | Left Eye | Right Eye |
| GROUP A<br>B.S.S<br>Balanced Salt Solution | 3 | None | 30μl of B.S.S. | Hazy Vitreous Large Fibrous Clot | Hazy Vitreous Large Fibrous Clot |
| GROUP B<br>25 I.U. of Hyaluronidase (ACS) | 3 | None | Hyaluronidase (ACS) 25 I.U. IN 30μL | Hazy Vitreous Large Fibrous Clot | Clear Vitreous |
| GROUP C<br>50 I.U. of Hyaluronidase (ACS) | 3 | None | Hyaluronidase (ACS) 50 I.U. IN 30μL | Hazy Vitreous Large Fibrous Clot | Clear Vitreous |
| GROUP D<br>75 I.U. of Hyaluronidase (ACS) | 3 | None | Hyaluronidase (ACS) 75 I.U. IN 30μL | Hazy Vitreous Large Fibrous Clot | Clear Vitreous |

FIG.4

Safety and Efficacy of Multiple-Dose Intravitreal Hyaluronidase (ACS) in Rabbit Eyes

| Group | | Number of Rabbits | Eye Treatments | | Results | |
|---|---|---|---|---|---|---|
| | | | Left Eye | Right Eye | Left Eye | Right Eye |
| GROUP A | Balanced Salt Solution | 3 | None | 30 μl of B.S.S. | Hazy Vitreous Large Fibrous Clot | Hazy Vitreous Large Fibrous Clot |
| GROUP B | 25 I.U. of Hyaluronidase (ACS) | 3 | None | Hyaluronidase (ACS) 25 I.U. IN 30μL | Hazy Vitreous Large Fibrous Clot | Clear Vitreous Retina Normal with Indirect Ophthalmoscope |
| GROUP C | 50 I.U. of Hyaluronidase (ACS) | 3 | None | Hyaluronidase (ACS) 50 I.U. IN 30μL | Hazy Vitreous Large Fibrous Clot | Clear Vitreous Retina with Indirect Ophthalmoscope |
| GROUP D | I.U. of Hyaluronidase (ACS) | 3 | None | Hyaluronidase (ACS) 75 I.U. IN 30μL | Hazy Vitreous Large Fibrous Clot | Clear Vitreous Retina Normal with Indirect Ophthalmoscope |

FIG.5

Hemorrhage Clearing Efficacy of Single Intravitreal Injection of Hyaluronidase (ACS) in Human Patients with Diabetic Retinopathy

| Patient | Vitreous Hemorrhage | Dose of Hyaluronidase (ACS) Injected | Subjective Visual Activity | | Time To Hemorrhage Clearance (Days Post Dose) |
|---|---|---|---|---|---|
| | | | Pre-Treatment | Post Treatment | |
| Female 54 Years Old | Left Eye of 4 Months Duration | 50 I.U | Finger Counting at 3 ft. Hazy Vitreous | 20/60 Clear Vitreous | 6 days |
| Female 65 Years Old | Long Eye Duration | 50 I.U. | 20/400 Hazy Vitreous | 20/200 Clear Vitreous | 16 Days |
| Female 58 Years Old | Left Eye 1 Year Duration | 50 I.U. | Finger Counting at 5 ft. Hazy Vitreous | 20/60 Clear Vitreous | 11 Days |
| Female 85 Years Old | Right Blind Eye Because of Optic Nerve Damage | 200 I.U. | Very Hazy Vitreous | Clear Vitreous | 8 Days |
| Female 60 Years Old | Left Eye Blind Because of Glaucoma | 70 I.U. | Very Hazy Vitreous | Clear Vitreous | 7 Days |
| Male 25 Years Old | Left Eye Penetrating Performation Severe Intravitreal Hemorrhage | 50 I.U. | Very Hazy Vitreous Light Perception Only | Clear Vitreous Hand Movement as 1.0 Ft. | 14 Days |

FIG.6

METHOD FOR ACCELERATING CLEARANCE OF HEMORRHAGIC BLOOD FROM THE VITREOUS HUMOR WITH HYALURONIDASE

FIELD OF THE INVENTION

The present invention relates generally to enzyme preparations for therapeutic administration to the eyes of humans or other mammals, and more particularly to a) a method for utilizing one or more enzymes to accelerate the rate at which hemorrhagic blood is cleared from the vitreous body of the mammalian eye and b) an improved hyaluronidase preparation for ophthalmic administration.

BACKGROUND OF THE INVENTION i. Anatomy of the Human Eye

In human beings, the anatomy of the eye includes a "vitreous body" which occupies approximately four fifths of the cavity of the eyeball, behind the lens. The vitreous body is formed of gelatinous material, known as the vitreous humor. Typically, the vitreous humor of a normal human eye contains approximately 99% water along with 1% macromolecules including; collagen, hyaluronic acid, soluble glycoproteins, sugars and other low molecular weight metabolites.

The retina is essentially a layer of nervous tissue formed on the inner posterior surface of the eyeball. The retina is surrounded by a layer of cells known as the choroid layer. The retina may be divided into a) an optic portion which participates in the visual mechanism, and b) a non-optic portion which does not participate in the visual mechanism. The optic portion of the retina contains the rods and cones, which are the effectual organs of vision. A number of arteries and veins enter the retina at its center, and splay outwardly to provide blood circulation to the retina.

The posterior portion of the vitreous body is in direct contact with the retina. Networks of fibrillar strands extend from the retina and permeate or insert into the vitreous body so as to attach the vitreous body to the retina.

ii. The Causes, Treatments and Clinical Sequelae Of Intravitreal Hemorrhage

Diabetic retinopathy, trauma and other ophthalmological disorders sometimes result in rupture or leakage of retinal blood vessels with resultant bleeding into the vitreous humor of the eye (i.e., "intravitreal hemorrhage). Such intravitreal hemorrhage typically manifests as clouding or opacification of the vitreous humor.

Intravitreal hemorrhage is sometimes, but not always, accompanied by tearing or detachment of the retina. In cases where the intravitreal hemorrhage is accompanied by a retinal tear or detachment, it is important that such retinal tear or detachment be promptly diagnosed and surgically repaired. Failure to promptly diagnose and repair the retinal tear or detachment may allow photoreceptor cells of the retina, in the region of the tear or detachment, to become necrotic. Such necrosis of the photoreceptor cells of the retina may result in loss of vision. Furthermore, allowing the retinal detachment to remain unrepaired for such extended period of time may result in further intravitreal hemorrhage and/or the formation of fibrous tissue at the site of the hemorrhage. Such formation of fibrous tissue may result in the formation of an undesirable fibrous attachment between the vitreous body and the retina.

The typical surgical procedure used for repair of retinal tears or detachment requires that the surgeon be able to look through the vitreous humor, to visualize the damaged region of the retina i.e., "transvitreous viewing of the retina").

When intravitreal hemorrhage has occurred, the presence of the hemorrhagic blood within the vitreous can cause the vitreous to become so cloudy that the surgeon is prevented from visualizing the retina through the vitreous. Such hemorrhagic clouding of the vitreous can take 6–12 months or longer to clear sufficiently to permit trans-vitreal viewing of the retina. However, in view of the potential complications which may result from delayed diagnosis or treatment of a retinal tear or detachment, it is generally not desirable to wait for such natural clearance of the hemorrhagic blood to occur.

Furthermore, even when the intravitreal hemorrhage is not accompanied by retinal tear or detachment, it is often difficult to verify that retinal tear or detachment has not occurred, because the hemorrhagic clouding of the vitreous prevents the physician from performing routine funduscopic examination of the retina. Moreover, the presence of hemorrhagic blood within the vitreous may significantly impair the patient's vision through the affected eye, and will continue to do so until such time as the hemorrhagic blood has been substantially or fully cleared.

Thus, the presence of hemorrhagic blood within the vitreous body causes multiple clinical problems including a) inability to visually examine and diagnose the site of the hemorrhage and/or any accompanying tear or detachment of the retina, b) full or partial impairment of vision in the affected eye and c) impairment or prevention of the performance of trans-vitreal surgical procedures of the type typically utilized to repair the site of hemorrhage and/or to repair any accompanying retinal tear or detachment.

In cases where intravitreal hemorrhage has resulted in substantial clouding or opacification of the vitreous, the treating physician may have the option to perform a procedure known as a vitrectomy, wherein all (or a portion of) the vitreous body is removed from the interior of the eye, and replaced with a clear liquid. The performance of such vitrectomy procedure is intended to allow the surgeon to visualize the retina sufficiently to proceed with the necessary retinal examination and/or surgical repair of the hemorrhage and any accompanying retinal tear or detachment. However, such vitrectomy procedures are highly skill-intensive, and are associated with several significant drawbacks, risks and complications. Among these drawbacks, risks and complications are the potential that the act of removing the vitreous will cause further detachment or tearing of the retina and/or that such removal of the vitreous will cause further hemorrhage from the already-weakened retinal blood vessels.

iii. Prior Ophthalmic Applications Of Hyaluronidase and Other Enzymes

In an effort to minimize the potential for causing further detachment or tearing of the retina during performance of vitrectomy, it has previously been proposed in U.S. Pat. No. 5,292,509 (Hageman), to inject certain protease-free glycosaminoglycanase enzymes into the vitreous body, to cause the vitreous body to become uncoupled or "disinserted" from the retina, prior to removal of the vitreous body. Such disinsertion or uncoupling of the vitreous body is purported to minimize the likelihood that further tearing or detachment of the retina will occur as the vitreous body is removed. Examples of specific protease-free glycosaminoglycanase enzymes which may be used to bring about this vitreal disinsertion purportedly include; chondroitinase ABC, chondroitinase AC, chondroitinase B, chondroitin 4-sulfatase, chondroitin 6-sulfatase, hyaluronidase and β-glucuronidase.

Although hyaluronidase enzyme has been known to be usable for various ophthalmic applications, including the vitrectomy adjunct application described in U.S. Pat. No.

5,292,509 (Hageman), published studies have indicated that the hyaluronidase enzyme may itself be toxic to the retina and/or other anatomical structures of the eye. See, *The Safety of Intravitreal Hyaluronidase;* Gottleib, J. L.; Antoszyk, A. N., Hatchell, D. L. and Soloupis, P., Invest Ophthalmol Vis Sci 31:11, 2345–52 (1990).

The ophthalmic toxicity of some hyaluronidase preparations has been confirmed by other investigators, who have proposed that such hyaluronidase preparations be used as a toxic irritant for causing experimentally-induced neovascularization of the eye, in animal toxicity models. see, *An Experimental Model of Preretinal Neovascularization in the Rabbit;* Antoszyk, A. N., Gottleib, J. L., Casey, R. C., Hatchell, D. L. and Machemer, R., Invest Ophthalmol Vis Sci 32:1, 46–51 (1991).

Unfortunately, it has not been previously known whether the reported therapeutic activities and toxicities of hyaluronidase are universally applicable to all hyaluronidase preparations, or whether such efficacies and/or toxicities are applicable only to hyaluronidase preparations containing certain excipient materials or to hyaluronidase enzymes derived from specific sources. This is an important consideration in view of the fact that the purity and characterization (e.g., molecular weight distribution) of the various hyaluronidase preparations used in the prior art may vary, depending on the source of the hyaluronidase and the solvents and/or other formulation components with which the hyaluronidase is combined.

iv. Purity and Characterization of Hyaluronidase Preparations Previously used for Ophthalmic Administration The term "hyaluronidase" is commonly used to describe a group of endo-β-glucuronidase enzymes which depolymerize certain mucopolysaccharides, such as hyaluronic acid. Myer, K. et al., *The Enzymes;* Vol. 4, 2d, Ed., pp 447, Academic Press, Inc., New York (1960).

Hyaluronidase causes hydrolysis of the endo-N-acetyl hexosaminic bonds of hyaluronic acid and of the chondroitin sulfate acids A and C, primarily to tetrasaccharide residues.

Significant evidence indicates that hyaluronidase enzymes derived from different sources differ in enzyme molecular weight distribution and in specific enzymatic activities. Such variability in molecular weight distribution and specific enzymatic activity are noteworthy considerations in view of the fact that hyaluronidase enzymes may be isolated from a variety of sources, including bovine testes, ovine testes, certain bacteria such as streptomyces and certain invertebrate animals such as leeches.

The Wydase® hyaluronidase preparation is reported to have been previously administered to the eyes of mammals for various clinical and experimental applications, including the treatment of glaucoma and the promotion of liquefaction of the vitreous body during vitrectomy procedures wherein the vitreous body is removed from the eye.

Although some hyaluronidase preparations have been reported to exhibit desirable therapeutic effects when injected into or administered topically to the eye, the potential toxicities of hyaluronidase and/or the thimerosal preservative are cause for concern regarding the safety of routine clinical administration of such, preparations by intraocular injection.

Accordingly, there exists a need in the art for the formulation and development of a new hyaluronidase preparation which may be administered to the eye at dosage levels which are sufficient to bring about optimal therapeutic effects, but which do not cause ocular toxicity.

Additionally, in view of the above-discussed problems associated with the slowness of natural clearance of hemorrhagic blood from the vitreous body, there exists a need in the art for the elucidation and development of new methods and procedures for accelerating the clearance of hemorrhagic blood from the vitreous body of the eye so as to permit trans-vitreal viewing of the posterior aspect of the eye, including the retina, without the need for removal of the vitreous body (i.e., total or partial vitrectomy).

SUMMARY OF THE INVENTION

The present invention provides a method for accelerating the clearance of hemorrhagic blood from the vitreous humor of a mammalian eye, wherein the method comprises the step of contacting, with the vitreous humor, an amount of an enzyme which is active to accelerate the clearance of hemorrhagic blood from the vitreous humor. Specific enzymes which may be administered to bring about the hemorrhage clearing effect of the present invention include β-glucuronidases such as hyaluronidase, keratinase, chondroitinase AC, chondroitinase B and chondroitinase ABC; chondroitin sulfatases such as chondroitin 4 sulfatase and chondroitin 6 sulfatase; matrix metalloproteinases such as matrix metalloproteinase 1, matrix metalloproteinase 2, matrix metalloproteinase 3 and matrix metalloproteinase 9; and protein-kinases such as streptokinase and urokinase.

Further in accordance with the present invention, there is provided an improved, thimerosal free, hyaluronidase preparation which is suitable for administration onto or within the eye as a therapeutic agent for the treatment of various disorders including, but not limited to, the acceleration of the clearance of hemorrhagic blood from the vitreous humor in accordance with the hemorrhage-clearing methodology of the present invention. This hyaluronidase preparation of the present invention comprises a preferred hyaluronidase enzyme which is substantially devoid of hyaluronidase molecules having molecular weights in excess of 100,000, between 60,000–70,000 and/or below 40,000. The preferred hyaluronidase of the present invention may be obtained from ovine testes, and may be combined in aqueous solution with quantities of lactose and phosphate, to provide a thimerosal-free aqueous hyaluronidase solution for intraocular injection.

Further objects and advantages of the present invention will become apparent to those skilled in the area upon reading and understanding of the following detailed description, the accompanying figures, and the examples set forth therein.

BRIEF DESCRIPTION OF THE DRAWINGS

FIG. 2 is a table which summarizes the zymographically determined hyaluronic acid lysing, gelatinolytic and caseinolytic activities of the hyaluronidase ACS of the present invention, in comparison to bovine hyaluronidases of types VI-S, IV-S and I-S and ovine hyaluronidase of type V.

FIG. 3 is a table which summarizes the toxic effects of single dose intravitreal injections of BSS, BSS+thimerosal, hyaluronidase (ACS) and hyaluronidase Wydase® in rabbits, in accordance with Example I herebelow.

FIG. 4 is a table which summarizes the efficacy of single-dose intravitreal hyaluronidase (ACS) in rabbits, in accordance with Example II herebelow.

FIG. 5 is a table which summarizes the safety and efficacy of multiple doses of intravitreal hyaluronidase (ACS) in rabbits, in accordance with Example III herebelow.

FIG. 6 is a table which summarizes the hemorrhage-clearing efficacy of single dose hyaluronidase ACS in human patients having diabetic retinopathy, in accordance with Example IV herebelow.

DETAILED DESCRIPTION OF THE PREFERRED EMBODIMENTS

Figure 1:
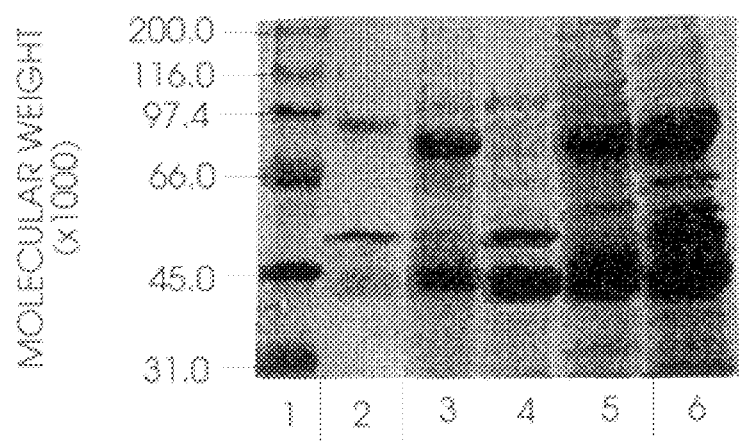
FIG. 1 shows an electrophoresis gel having lanes 1–6, said lanes indicating 1) molecular weight standards from 31,000 through 200,000 2) ovine hyaluronidase (ACS), 3) bovine hyaluronidase type VI-S, 4) ovine hyaluronidase type V, 5) bovine hyaluronidase type IV-S and 6) bovine hyaluronidase type I-S.

The following detailed description and the accompanying examples are provided for purposes of describing and explaining certain preferred embodiments of the invention only, and are not intended to limit the scope of the invention in any way.

i. Enzymatic Method For Accelerating Clearance Of Hemorrhagic Blood From the Vitreous of the Eye In accordance with the invention, applicant has determined that certain types of enzymes, when contacted with the vitreous humor following hemorrhage thereinto, will accelerate the rate at which the hemorrhagic blood is cleared from the vitreous humor.

In this regard, Applicant has devised a method for accelerating clearance of hemorrhagic blood from the vitreous of the eye, said method generally comprising the step of contacting, with the vitreous humor, at least one enzyme in an amount which is active to accelerate the clearance of hemorrhagic blood from the vitreous humor. This hemorrhage-clearing method of the present invention may be performed without any vitrectomy or other surgical manipulation or removal of the vitreous humor, thereby avoiding the potential risks and complications associated with such vitrectomy procedures.

Specific β-glucuronidase enzymes which exhibit this hemorrhage-clearing effect include:

Hyaluronidase
Keratinase
Chondroitinase AC
Chondroitinase B
Chondroitinase ABC
Chondroitin 4 sulfatase; and
Chondroitin 6 sulfatase Specific metalloproteinase enzymes which exhibit this hemorrhage-clearing effect include:

Matrix Metalloproteinase-1
Matrix Metalloproteinase-2
Matrix Metalloproteinase-3
Matrix Metalloproteinase-9

Specific protein-kinase enzymes which exhibit this hemorrhage-clearing effect include:

Streptokinase
Urokinase

The preferred route of administration of these hemorrhage-clearing enzymes is by intraocular injection. whereby an injectable solution containing one or more of the above-listed hemorrhage clearing enzymes is injected, through a needle, directly into the vitreous body located within the posterior chamber of the eye. Alternatively, however, the hemorrhage-clearing enzyme(s), of the present invention may be administered by any other suitable route of administration (e.g., topically) which results in sufficient distribution of the enzyme(s) to the vitreous body to cause the desired hemorrhage-clearing effect.

The preferred injectable solution of the hemorrhage-clearing enzyme(s) may contain, in addition to the hemorrhage-clearing enzyme(s), certain inactive ingredients which cause the solution to be substantially isotonic, and of a pH which is suitable for injection into the eye. Such solution for injection may be initially lyophilized to a dry state and, thereafter, may be reconstituted prior to use.

ii. A Preferred Hyaluronidase Preparation For Ophthalmic Administration

A general formulation for an injectable thimerosal-free, hyaluronidase preparation, of the present invention is shown in Table I as follows:

TABLE I

General Formulation

| Ingredient | Quantity |
|---|---|
| Hyaluronidase (ACS) | up to 8000 International units |
| Lactose, USP | 13.3 mg–133.0 mg |
| Phosphate, USP | 5–200 mmoles |

These formulation ingredients are initially dissolved in sterile water, sterile filtered and subsequently lyophilized to a dry composition. The lyophilized composition is packaged for subsequent reconstitution prior to use, in balanced salt solution. Such balanced salt solution typically contains: 0.64% sodium chloride, 0.075% potassium chloride, 0.048% calcium chloride dihydrate, 0.03% magnesium chloride hexahydrate, 0.39% sodium acetate trihydrate, 0.17% sodium citrate dihydrate, sodium hydride/hydrochloric acid to adjust the pH, and water for injection qs 100%.

The term "hyaluronidase ACS" as used herein describes a preferred hyaluronidase which is devoid of hyaluronidase molecular weight fractions above 100,000, between 60,000–70,000 and below 40,000. Such hyaluronidase may be derived from ovine testicles and is available commercially from Calbiochem Biochemicals, P.O. Box 12087, La Jolla, Calif. 92039-2087. Applicants have determined that this specific molecular weight distribution of the hyaluronidase ACS results in less ophthalmic toxicity than other hyaluronidase preparations, while exhibiting desirable therapeutic efficacy in a number of ophthalmic applications.

FIG. 1 shows an electrophoresis gel (10% SDS-PAGE) which demonstrates the molecular weight distribution of the preferred hyaluronidase ACS in comparison to the molecular weight distributions of bovine type VI-S, IV-S and I-S and ovine type V hyaluronidases obtained from Sigma Chemical Company, P.O. Box 14508, St. Louis, Mo. 63178. Standardized amounts (i.e., equivalent units of hyaluronidase activity) of each enzyme was loaded into each lane (lanes 2–6) of the electrophoresis gel shown in FIG. 1. Lane 1 of the electrophoresis gel shown in FIG. 1 contains molecular weight markers at 200,000, 116,000, 97,400, 66,000, 45,000, and 31,000 mw, respectively. Lanes 2–6 of the electrophoresis gel shown in FIG. 1 contain the respective hyaluronidase preparations tested, as follows:

| LANE | WHAT IS IN THE LANE |
|---|---|
| 2 | Hyaluronidase ACS |
| 3 | Bovine Hyaluronidase type VI-S |
| 4 | Ovine Hyaluronidase type V |
| 5 | Bovine Hyaluronidase type IV-S |
| 6 | Bovine Hyaluronidase type I-S |

Lane 2 shows that the molecular weight distribution of the hyaluronidase ACS includes molecular weight fractions of 97,400, 50,000 (approx.) and 45,000 (approx.), but is clearly devoid of molecular weight fractions above 100,000, between 60,000–70,000 and below 40,000.

Lanes 3, 4, 5 and 6 of the electrophoresis gel of FIG. 1 show that all of the bovine testicular hyaluronidases of types VI-S, IV-S and I-S and ovine testicular hyaluronidase of type V tested differ from the hyaluronidase ACS of the present invention in that they include molecular weight fractions between 60,000–70,000 and below 40,000. Also, three (3) of the four (4) bovine testicular hyaluronidases tested (i.e., types VI-S, IV-S and I-S) included hyaluronidase molecular weight fractions which were in excess of 100,000.

Additionally, zymograms were performed to compare the relative lytic activities of standardized amounts (i.e., equivalent units of hyaluronidase activity) of the above-described hyaluronidase ACS, type VI-S, V, IV-S and I-S bovine hyaluronidases upon hyaluronic acid, gelatin and casein. With respect to FIG. 2, the specific methods by which each of these zymograms was performed are as follows:

Zymogram for Gelatinolytic Activity

GELATIN—1 mg/ml gelatin; 10% polyacrylamide; overnight buffer=50 mM Tris HCl, 5 mM $CaCl_2$, 0.05% TritonX-100 pH 7.5; stain Coomassie blue; destain 10% acetic acid/50% methanol.

Zymogram for Caseinolytic Activity

CASEIN-4 mg/ml; 15% polyacrylamide; overnight buffer=50 mM Tris/HCl, 5 mM $CaCl_2$ and 0.05% Triton X-100 pH 7.5; stain Coomassie blue; destain 10% acetic acid/50% methanol Zymogram for Hyaluronic Acid Lysing Activity HYALURONIC ACID 2 mg/ml, 10% polyacrylamide; overnight buffer=phosphate buffered saline, pH 7.4; stain 0.5% alcian blue in 3% acetic acid; destain 10% acetic acid/50% methanol The results of these hyaluronic acid, gelatin and casein zymograms are summarized in the table of FIG. 2. Notably, the preferred hyaluronidase ACS of the present invention is devoid of hyaluronic acid lysing molecular weight fractions above approximately 100,000 while each of the bovine testicular hyaluronidases tested (i.e., types VI-S, IV-S and I-S) contained hyaluronic acid lysing molecular weight fractions above 100,000.

Similarly, the hyaluronidase ACS of the present invention was devoid of gelatinolytic molecular weight fractions between approximately 60,000–100,000, while each of the bovine testicular hyaluronidases tested included gelatinolytic molecular weight fractions between approximately 60,000–100,000.

Also, the hyaluronidase ACS of the present invention was devoid of caseinolytic molecular weight fractions above approximately 45,000 while each of the bovine testicular hyaluronidases (i.e., types VI-S, IV-S and I-S) and ovine testicular hyaluronidase (type V) tested did contain caseinolytic molecular weight fractions above approximately 45,000.

The specific molecular weight distribution and specific enzyme activity profile of the preferred hyaluronidase (ACS) of the present invention, and/or the exclusion of thimerosal from its formulation, provides a hyaluronidase preparation which is non-toxic to the eye when administered at dosage levels at which other hyaluronidase preparations would cause toxic effects.

For use in the examples set forth herebelow, the preferred hyaluronidase ACS was prepared in a thimerosal free formulation by the method and general formula described herebelow and shown in Table I. More specifically, the hyaluronidase used in the following examples prepared in accordance with the specific formulation shown in Table II herebelow.

TABLE II

Specific Formulation

| Ingredient | Quantity |
| --- | --- |
| Hyaluronidase (ACS) | 7,200 I.U. |
| Lactose USP | 13.3 mg |
| Phosphate USP | 5 mmoles |

As described in the following examples, the specific preferred formulation as hyaluronidase ACS set forth in Table II (above) may be injected directly into the posterior chamber of the eye at dosage levels which bring about desirable therapeutic affects, including but not necessarily limited to the intravitreal hemorrhage clearing effect of the present invention, without causing significant toxicity to the eye or associated anatomical structures.

EXAMPLE I

Ophthalmic Toxicities of Thimerosal, Hyaluronidase (ACS) and Hyaluronidase (Wydase®) in Rabbits fifty-two (52) healthy rabbits of the New Zealand Cross variety (26 male, 26 female) weighing 1.5 kg to 2.5 kg, were individually marked for identification and were housed individually in suspended cages. The animals received a commercially available pelleted rabbit feed on a daily basis, with tap water available ad libitum.

The animals were divided into thirteen groups of 4 animals each (2 male, 2 female). Two animals in each group (1 male, 1 female) were selected for pretreatment fundus photography and fluorescein angiography.

The fundus photography was performed by restraining the animals and visualizing the optic nerve, retinal arcades and fundas with a KOWA® RC-3 Fundus Camera loaded with Kodak Gold 200 ASA film.

The fluorescein angiography involved a 1.5 ml injection of 2% sterile fluorescein solution via the marginal ear vein. Approximately 30 seconds post-injection the fluorescein was visualized upon localization of the optic nerve, retinal vessels and fundas.

The following day, each animal was anesthetized by intravenous administration of a combination of 34 mg/kg of ketamine hydrochloride and 5 mg/kg xylazine. The eyelids were retracted using a lid speculum, and the eyes were disinfected with an iodine-providone wash.

Experimental treatments of either balanced salt solution (BSS), BSS+thimerosal, hyaluronidase (Wydase®) or hyaluronidase (ACS) were administered by injection using a 1 cc tuberculin syringe with a 30 guage, 0.5 inch needle attached thereto. The hyaluronidase (ACS) solution utilized in this example was free of thimerosal and constituted the specific preferred hyaluronidase ACS formulation set forth in Table II hereabove.

The experimental treatments administered to each animal group were as follows:

| Group # | Treatment |
|---|---|
| 1 | BSS |
| 2 | BSS + 0.0075 mg Thimerosal |
| 3 | BSS + 0.025 mg Thimerosal |
| 4 | Hyaluronidase (Wydase) 1 IU |
| 5 | Hyaluronidase (Wydase) 15 IU |
| 6 | Hyaluronidase (Wydase) 30 IU |
| 7 | Hyaluronidase (Wydase) 50 IU |
| 8 | Hyaluronidase (Wydase) 150 IU |
| 9 | Hyaluronidase (ACS) 1 IU |
| 10 | Hyaluronidase (ACS) 15 IU |
| 11 | Hyaluronidase (ACS) 30 IU |
| 12 | Hyaluronidase (ACS) 50 IU |
| 13 | Hyaluronidase (ACS) 150 IU |

The day following the injections (Day 1), the 26 animals which were subjected to the fundus photography and fluorescein angiography were observed using the same methods as for the predose examination.

On Day 2 following the injections, the 13 male rabbits that had received the fundus photography and fluorescein angiography at predose and Day 1, as well as the 13 female rabbits that were not selected for photography were euthanized with a sodium pentobarbital based drug. The eyes were then surgically removed and placed in a fixture solution of 2.5% glutaraldehyde with 0.1M phosphate buffered saline at pH 7.37.

Alternatively, one randomly selected rabbit was euthanized by pentobarbital injection but then fixed by intracardiac injection of the glutaraldehyde solution into the left ventricle to determine the effect of the fixation procedure on the histology findings within the enucleated eyes.

On Day 7, the 13 female rabbits that had been previously photographed and angiography performed were subjected to the same observations following the methods previously described.

The remaining 26 animals were euthanized as described above 7 days after dosing. The eyes were fixed in the same manner as those which had been fixed on day 2. Also, one randomly selected rabbit was subjected to the same intracardiac glutaraldehyde fixation procedure described hereabove for the previously randomly selected animal.

The eyes of the animals treated in this example were examined grossly and microscopically for evidence of treatment-related toxicities. A table setting forth a summary of the histological evidence of toxicity or non-toxicity in each treatment group, is set forth in FIG. 3.

In summary, the eyes of the BSS-treated control group were free of toxicity at 2 and 7 days post dose.

The eyes of the Group No. 2 animals treated with BSS+ thimerosal (0.0075 mg) were free of toxicity at day 2, but exhibited evidence that there was a breakdown of the blood-retinal barrier at day 7.

The Group No. 3 animals treated with BSS+thimerosal (0.025 mg) exhibited severe treatment-related toxic effects, at days 2 and 7 post dose.

The Group No. 4 animals treated with Wydase® at the 1 I.U. dose were free of toxicity at days 2 and 7, however, the eyes of the animals in Group Nos. 5–8 treated with Wydase® at dosages ranging from 15 I.U.–150 I.U. exhibited generally dose-related toxic effects at days 2 and 7 post dose.

The eyes of animals in treatment Groups Nos. 9–13 treated with hyaluronidase (ACS) at dosages ranging from 1 I.U. through 150 I.U., were free of evidence of toxic effects at days 2 and 7 post dose.

Accordingly, it is concluded that thimerosal and the thimerosal-containing Wydase® formulation do cause toxic effects in the eyes of rabbits at the dosages tested, however, hyaluronidase (ACS) caused no toxic effects in these animals at the dosages tested.

The results of the examinations conducted on day 7 are summarized in FIG. 3. As shown in FIG. 3, significant toxic effects were observed on day 7 in the eyes of rabbits treated with BSS plus thimerosal (0.0075 mg) and hyaluronidase (Wydase) at all doses between 1 I.U.–150 I.U. In contrast, no toxic effects were observed in the eyes of animals treated with hyaluronidase (ACS) at doses between 1–50 I.U.

EXAMPLE II

Safety and Efficacy of Hyaluronidase (ACS) Injected Intravitreally in Rabbit Eyes In this example, 12 healthy rabbits of the New Zealand Cross variety were marked for identification and individually housed in suspended cages. The animals received commercially pelleted rabbit feed on a daily basis and tap water was available ad libitum.

The animals were randomly divided into four (4) treatment groups of three (3) animals each.

Initially, the eyes of each animal were examined by dilation with 1–2 drops of 10% tropicanide followed by gross examination, indirect ophthalmoscopy using a 20 diopter lens, and slit lamp examination of the anterior anatomy of the eye.

Following the initial examination of the animals' eyes, 100 μl or 10 μl of blood was injected intravitreally into each eye of each animal.

On day 2, the animals of each treatment group received a single intravitreal injection of either BSS or Hyaluronidase (ACS) into the right eye, in accordance with the following treatment schedule:

| | Treatment | |
|---|---|---|
| Group # | Left Eye | Right Eye |
| A | None | BSS (30 μl) × 1 |
| B | None | 25 I.U. Hyaluronidase (ACS) in 30 μl × 1 |
| C | None | 50 I.U. Hyaluronidase (ACS) in 30 μl × 1 |
| D | None | 75 I.U. Hyaluronidase (ACS) in 30 μl × 1 |

The hyaluronidase (ACS) preparation used in this experiment was the preferred formulation described hereabove and shown in Table II.

On days 3, 5, 7, 14 and 21 the eyes of each animal were again examined by slit-lamp to evaluate the cornea, anterior chamber and iris. In addition, the eyes of each animal were dilated with 10% tropicamide solution and the retina was examined by indirect ophthalmoscopy with a 20 dioptor lens.

The observed hemorrhage-clearing efficacy of hyaluronidase ACS is summarized in FIG. 4. In general, the left eye (untreated) of each animal in each treatment group contained hazy vitreous and some blood clots, due to the quantity of blood which had been injected therein. The right eyes of the BSS treated (control) animals of Group A also contained hazy vitreous and some blood clots, while the right eyes of all hyaluronidase-treated animals in Treatment Groups B–D contained vitreous which was clear and through which transvitreal visualization of the retina was possible. Furthermore, the retinas of the right eyes of all animals in Treatment Groups B-D appeared normal and free of treatment-related toxicity.

The results of this experiment indicate that intravitreally administered hyaluronidase (ACS) was effective at single doses of 25–75 I.U., to accelerate the rate at which blood was cleared from the eyes of the treated animals and further that such single doses of hyaluronidase (ACS) administered in this experiment did not cause observable toxic effects in the eyes of the rabbits treated in this experiment.

The observations following each dose were consistent and are summarized in FIG. 5. In general, the left eye (untreated) of each animal in each treatment group, contained hazy vitreous humor and some blood clots, due to the quantity of blood which had been injected therein. The right eyes of the BSS treated (control) animals of Group A also contained hazy vitreous and some blood clots, while the right eyes of all animals in treatment Groups B–E (i.e., the animals treated with hyaluronidase (ACS)) contained clear vitreous through which transvitreal visualization of the retina was possible. Furthermore, the retinas of the right eyes of all animals in treatment Groups B–D appeared to be normal and free of treatment-related toxicity, even after multiple doses of the hyaluronidase ACS.

The results of this experiment indicate that intravitreally administered hyaluronidase (ACS) was effective, at single doses of 25–75 I.U.×4, to accelerate the rate at which blood was cleared from the eyes of rabbits and further that such dosages of hyaluronidase (ACS), and that such doses of hyaluronidase ACS did not cause observable toxic effects in the eyes of the treated rabbits, even after four (4) consecutive doses of hyaluronidase ACS administered at 2 week intervals.

EXAMPLE III

Hemorrhage Clearing Efficacy of Hyaluronidase (ACS) in Humans

In this experiment, six (6) human patients (5 female, 1 male) who presented with intravitreal hemorrhage were treated with single intravitreal injections or Hyaluronidase (ACS) at dosages of 50–200 I.U.

The Hyaluronidase (ACS) administered in this experiment was prepared by the preferred formulation described hereabove and shown in Table II.

All of the patients treated in this experiment had a history of diabetic retinopathy, and were found to have intravitreal hemorrhages of varying duration. In each patient, the amount of blood present in the vitreous was sufficient to prevent viewing of the retina by standard funduscopic means.

Each patient received a single intravitreal injection of hyaluronidase (ACS). Four (4) patients received a dose of 50 I.U., one (1) patient received a dose of 70 I.U., and one patient received a dose of 200 I.U.

The observed results of this experiment are summarized in FIG. 6.

In the six (6) patients treated in this example, the hemorrhagic vitreous became sufficiently clear to permit transvitreal viewing of the retina within 6–16 days of the single intravitreal injection of the hyaluronidase (ACS). Such clearing of the vitreous was subjectively determined to have occurred significantly faster than that which would have been expected to occur in these patients without hyaluronidase treatment.

The foregoing detailed description, examples, and accompanying figures have described the present invention with reference to certain presently preferred embodiments thereof. It will be appreciated by those skilled in the art that various deviations may be made from the specific embodiments and formulations described hereabove, without departing from the intended spirit and scope of the present invention. Accordingly, it is intended that all such reasonable deviations be included within the scope of the following claims.

What is claimed is:

1. A method for accelerating the clearance of hemorrhagic blood from the vitreous humor of a mammalian eye, said method comprising the step of;

injecting into the vitreous humor a solution which contains hyaluronidase to provide a dose of at least 15 International Units of hyaluronidase, said solution being:
  i) free of thimerosal;
  ii) essentially devoid of hyaluronic acid-lysing material having a molecular weight greater than 100,000;
  iii) essentially devoid of caseinolytic material having a molecular weight greater than 45,000; and,
  iv) essentially devoid of gelatinolytic material having a molecular weight between 60,000 and 100,000.

2. The method of claim 1 wherein the dose of hyaluronidase is 50–200 International Units.

3. The method of claim 2 wherein the dose of hyaluronidase is 25–75 International Unit.

4. The method of claim 2 wherein the dose of hyaluronidase is 25 International Units.

5. The method of claim 2 wherein the dose of hyaluronidase is 50 International Units.

6. The method of claim 2 wherein the dose of hyaluronidase is 70 International Units.

7. The method of claim 2 wherein the dose of hyaluronidase is 200 International Units.

8. The method of claim 1 wherein said step is performed a single time, thereby resulting in the injection into the vitreous humor of a single dose of at least 15 International Units of said hyaluronidase.

9. The method of claim 1 wherein said step is performed at least twice, thereby resulting in the injection into the vitreous humor of at least two separate doses of said hyaluronidase, each dose being at least 15 International Units.

* * * * *